United States Patent
Torii et al.

(10) Patent No.: US 9,649,022 B2
(45) Date of Patent: May 16, 2017

(54) CONTROL METHOD OF A FUNDUS EXAMINATION APPARATUS

(71) Applicant: NIDEK CO., LTD., Gamagori-shi, Aichi (JP)

(72) Inventors: Hisanari Torii, Gamagori (JP); Toshio Murata, Milpitas, CA (US); Naoyuki Kondoh, Anjo (JP)

(73) Assignee: NIDEK CO., LTD., Gamagori (JP)

( * ) Notice: Subject to any disclaimer, the term of this patent is extended or adjusted under 35 U.S.C. 154(b) by 164 days.

(21) Appl. No.: 14/570,970

(22) Filed: Dec. 15, 2014

(65) Prior Publication Data

US 2015/0103316 A1 Apr. 16, 2015

Related U.S. Application Data

(63) Continuation of application No. 13/288,610, filed on Nov. 3, 2011, now Pat. No. 8,931,904.

(30) Foreign Application Priority Data

Nov. 5, 2010 (JP) .................................. 2010-249228
Nov. 5, 2010 (JP) .................................. 2010-249229

(51) Int. Cl.
*A61B 3/02* (2006.01)
*A61B 3/00* (2006.01)
(Continued)

(52) U.S. Cl.
CPC .......... *A61B 3/0058* (2013.01); *A61B 3/0025* (2013.01); *A61B 3/024* (2013.01);
(Continued)

(58) Field of Classification Search
CPC ..... A61B 3/0058; A61B 3/0091; A61B 3/024; A61B 3/1225; A61B 3/1241; A61B 3/18; A61B 3/12
(Continued)

(56) References Cited

U.S. PATENT DOCUMENTS 3,883,235 A 5/1975 Lynn et al.
6,705,726 B2 3/2004 Tanassi et al.
(Continued)

FOREIGN PATENT DOCUMENTS

EP 1 894 518 A1 3/2008
JP A-H03-202043 9/1991
(Continued)

OTHER PUBLICATIONS

Menke et al., "Combined use of SLO microperimetry and OCT for retinal functional and structural testing," *Graefe's Archive for Clinical and Experimental Ophthalmology*, vol. 244, No. 5, pp. 634-638, Aug. 25, 2005.

(Continued)

*Primary Examiner* — Huy K Mai
(74) *Attorney, Agent, or Firm* — Oliff PLC

(57) ABSTRACT

A control method of a fundus examination apparatus constructed as a perimeter for examining a fundus of an examinee's eye, includes: controlling a monitor provided in the fundus examination apparatus as the perimeter to display a two-dimensional map pertinent to a two-dimensional analysis result of the fundus based on a tomographic image of the examinee's eye obtained by an optical coherence tomography device; setting an examination position in the fundus examination apparatus as the perimeter on the two-dimensional map displayed on the monitor; and controlling the fundus examination apparatus as the perimeter based on the set examination position to examine the fundus.

9 Claims, 10 Drawing Sheets

(51) Int. Cl.
    *A61B 3/12*     (2006.01)
    *A61B 3/024*     (2006.01)
    *A61B 3/10*     (2006.01)
    *A61B 3/18*     (2006.01)

(52) U.S. Cl.
    CPC ................ *A61B 3/102* (2013.01); *A61B 3/12* (2013.01); *A61B 3/1225* (2013.01); *A61B 3/18* (2013.01)

(58) Field of Classification Search
    USPC .................................. 351/205, 206, 224, 246
    See application file for complete search history.

(56) References Cited

U.S. PATENT DOCUMENTS

| | | |
|---|---|---|
| 7,367,674 B2 | 5/2008 | Kirchhuebel |
| 7,510,282 B2 | 3/2009 | Ueno et al. |
| 7,641,339 B2 | 1/2010 | Hangai et al. |
| 2005/0280776 A1 | 12/2005 | Suzuki |
| 2010/0039616 A1 | 2/2010 | Yumikake et al. |
| 2010/0220914 A1 | 9/2010 | Iwase et al. |
| 2011/0046480 A1* | 2/2011 | Yonezawa ............ A61B 3/102 600/425 |
| 2011/0137157 A1* | 6/2011 | Imamura ............ G06T 7/0012 600/425 |
| 2011/0286003 A1 | 11/2011 | Ono |

FOREIGN PATENT DOCUMENTS

| | | |
|---|---|---|
| JP | A-2003-235800 | 8/2003 |
| JP | A-2005-342107 | 12/2005 |
| JP | A-2006-280665 | 10/2006 |
| JP | A-2008-029467 | 2/2008 |
| JP | A-2009-034480 | 2/2009 |
| JP | A-2009-089792 | 4/2009 |
| JP | A-2010-181172 | 8/2010 |
| JP | A-2010-200918 | 9/2010 |
| WO | WO 2008129863 A1 | 10/2008 |
| WO | WO 2009/073970 A1 | 6/2009 |
| WO | WO 2010/013378 A1 | 2/2010 |
| WO | WO 2010119596 A1 | 10/2010 |

OTHER PUBLICATIONS

European Search Report issued in Application No. 11187640.5; Dated Feb. 24, 2012.

* cited by examiner

```
              23  26 | 25  25
          26  26  32 | 26  26  28
      32  25  29  23 | 26  31  25  27
W2 ┌─────┐
   │18  17│30  28  19 | 22  19  29  28  30
   │18  16│28  26  24 | 30  27   0  29  28
   └─────┘─────────────────────────────────
      24  29  24  31  32 | 32  30   0  25  30
      27  27  30  28  28 | 31  31  29  28  27
          29  28  29  30 | 27  30  32  25
              26  27  31 | 28  28  28
                  24  25 | 26  29
```

CONTROL METHOD OF A FUNDUS EXAMINATION APPARATUS

CROSS-REFERENCE TO RELATED APPLICATIONS

This application is a continuation application of U.S. patent application Ser. No. 13/288,610 filed on Nov. 3, 2011, which is in turn based upon and claims the benefit of priority from the prior Japanese Patent Applications No. 2010-249228 filed on Nov. 5, 2010 and No. 2010-249229 filed on Nov. 5, 2010. The entire contents of each of the above-described applications are incorporated herein by reference.

TECHNICAL FIELD

The present invention relates to a control method of a fundus examination apparatus configured to examine the fundus of an examinee's eye.

BACKGROUND ART

A fundus imaging apparatus (an optical coherence tomography device) uses the technique of optical coherence tomography (OCT) to obtain tomographic images of an ophthalmic fundus. The obtained tomographic images are used to determine the condition of an eye to be examined (see the Patent Document 1).

A perimeter is an apparatus used for a subjective measurement of a patient's visual field, wherein the visual field is measured by confirming whether the examined patient can visually recognize a target set for examination (see the Patent Document 2).

An apparatus disclosed in the Patent Document 3 is capable of capturing color images of a fundus, wherein an examiner projects a target on an affected site of a subject's eye while watching the color images of the fundus to check the subject's visual field. A problem of the apparatus is complexity in use because the visual field has to be examined depending on the shape or size of the affected site (fundus abnormality).

RELATED ART DOCUMENTS

Patent Documents

Patent Document 1: JP 2008-29467 A (U.S. Pat. No. 7,510,282)
Patent Document 2: JP 2006-280665 A
Patent Document 3: JP 2003-235800 A (U.S. Pat. No. 6,705,726)

DISCLOSURE OF THE INVENTION

Problems to be Solved by the Invention

There are a number of differences between the fundus imaging apparatus and the perimeter in respect to optical systems, examination methods, and examination results. Therefore, if an examiner is not familiar with these apparatuses, he/she may perform unnecessary examinations or needs more time for examinations than originally intended.

To solve the above problems, an object of the present invention is to provide a fundus examination apparatus in which a fundus imaging apparatus can be used cooperatively with a perimeter.

Means of Solving the Problems

To achieve the object, one aspect of the present invention provides a control method of a fundus examination apparatus configured to examine a fundus of an examinee's eye, the method including: processing an examination data obtained by one of fundus examination apparatuses, which are a perimeter configured to measure a visual field and an optical coherence tomography device configured to obtain a tomographic image of the fundus, to thereby obtain positional information relating to an abnormal site of the fundus; setting an examination position on the fundus in the other fundus examination apparatus which is the perimeter or the optical coherence tomography device based on the positional information; and examining the abnormal site of the fundus by controlling the other fundus examination apparatus based on the set examination position.

Effects of the Invention

According to the invention, a fundus imaging apparatus and a perimeter can be used cooperatively.

MODE FOR CARRYING OUT THE INVENTION

<Method of Controlling Optical Coherence Tomography Based on Perimeter Examination Result>

Hereinafter, a first embodiment of the present invention will be described referring to the accompanied drawings.

Figure 1:
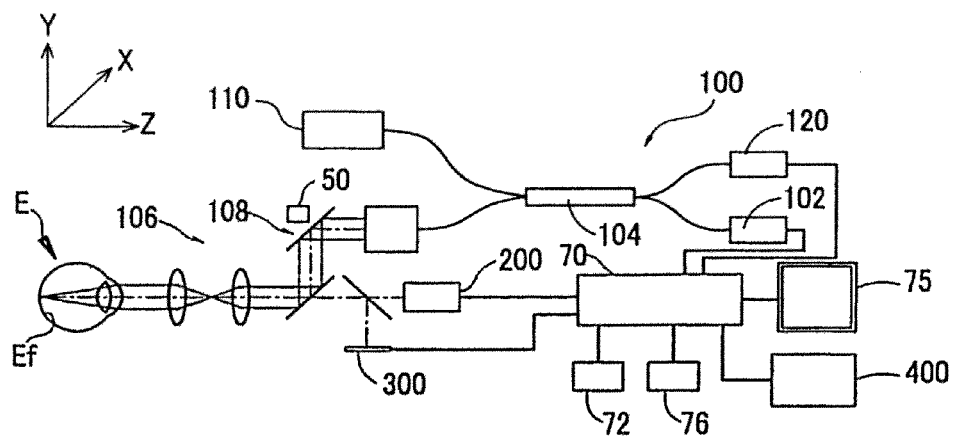
FIG. 1 is a block diagram to explain the configuration of a fundus examination apparatus in a first embodiment.

FIG. 1 is a block diagram illustrating a structure of a fundus examination apparatus according to the present embodiment. In the description of the present embodiment hereinafter given, an axial direction of an examinee's eye (eye E) is referred to as a Z direction, a horizontal direction thereof is referred to as an X direction, and a vertical direction thereof is referred to as a Y direction.

The structure of the fundus examination apparatus (which is a fundus imaging apparatus in the present embodiment) is schematically described. The fundus imaging apparatus is provided with an imaging position setting unit (for example, a control unit 70) which sets a tomographic image capturing position in an optical coherence tomography device (for example, an OCT optical system 100) configured to capture tomographic images of a fundus Ef. The imaging position setting unit acquires a measurement result data obtained when a visual field of the eye E is measured by a perimeter 400, and sets an imaging positional information on the fundus based on the acquired measurement result data.

The OCT optical system 100 is provided with an irradiation position changing unit (for example, an optical scanner 108, a fixation target projecting unit 300) configured to change an irradiating position of measurement light emitted from a light source 102 onto the fundus in order to change the tomographic image capturing position on the fundus Ef. The OCT optical system 100 detects a state of coherence between the measurement light reflected from the fundus and reference light from a light receiving element (a detector 120) and thereby captures a tomographic image of the fundus. The control unit 70 obtains the tomographic image based on a light-received signal output from the light receiving element by controlling the operation of the irradiation position changing unit based on the set imaging positional information.

Hereinafter, the structure of the fundus imaging apparatus is described in detail. The fundus imaging apparatus includes an optical coherence system (OCT optical system) 100 configured to capture tomographic images of the fundus Ef, a front observation optical system 200 configured to capture front images of the fundus Ef, a fixation target projecting unit 300 capable of fixating the eye E and changing a direction where the eye E is fixated, and a calculation and control unit (CPU) 70 which controls each component of the respective configurations 100 to 300. For example, refer to JP2008-29467A for more details of the fundus imaging apparatus.

The control unit 70 obtains the tomographic image (OCT images) by image processing based on the light-received signal output from the detector 120 of the OCT optical system 100, and also obtains the front image based on a light-received signal output from a light receiving element of the front observation optical system 200. Further, the control unit 70 changes a fixation position by controlling the fixation target projecting unit 300.

A memory (a storage part) 72, a monitor 75, a mouse (an operation input part) 76, and the perimeter 400 are all electrically connected to the control unit 70. The control unit 70 controls the operations of the respective devices or parts in accordance with a fundus imaging program and other control programs stored in the memory 72. When the fundus imaging program is run on a computer, the fundus imaging apparatus can be used.

The control unit 70 controls a display screen of the monitor 75 in accordance with the fundus imaging program. The obtained fundus image is output as a still image or a moving image to the monitor 75 and also stored in the memory 72.

Other than the capability of displaying the captured images and measurement results variously obtained on the monitor 75, the fundus imaging program in the present embodiment has an analysis mode function for analyzing a measurement data obtained by the perimeter to identify any abnormal site of the fundus Ef. The control unit 70 controls the OCT optical system 100, front observation optical system 200, and fixation target projecting unit 300 based on operation signals output by way of the mouse 76.

The OCT optical system 100 is an apparatus configured for ophthalmic optical coherence tomography (OCT). The OCT optical system 100 splits the light emitted from the light source 102 into a measurement light beam and a reference light beam by using a coupler (a light splitter) 104. The OCT optical system 100 guides the measurement light beam to the fundus Ef of the eye E by way of a measurement optical system 106, and further guides the reference light beam to a reference optical system 110. Then, the OCT optical system 100 makes the detector (light receiving element) 120 receive a coherent light which is a synthesis result of the measurement light reflected from the fundus Ef and the reference light.

The detector 120 detects the coherent light depending on the state of coherence between the measurement light and the reference light. In the case of Fourier-domain OCT, a spectral intensity of the coherent light is detected by the detector 120 and subjected to Fourier transform so that a depth profile in a predetermined range is obtained. Other examples of the OCT are Spectral-domain OCT (SD-OCT), Swept-source OCT (SS-OCT), and Time-domain OCT (TD-OCT).

In the case of SD-OCT, a low-coherent light source (a broadband light source) is used as the light source 102, and a spectral optical system (a spectrometer) configured to disperse the coherent light into different frequency components (wavelength components) is provided in the detector 120. The spectrometer includes, for example, a diffraction grating and a line sensor.

In the case of SS-OCT, a wavelength scanning light source (a wavelength variable light source) configured to change an emission wavelength very fast is used as the light source 102, and a light receiving element alone, for example, is used as the detector 120. The light source 102 includes, for example, a light source, a fiber ring resonator, and a wavelength selectable filter. Examples of the wavelength selectable filter are a filter in which a diffracting grating and a polygonal mirror are combined, and a filter in which Fabry-Perot etalon is used.

The light emitted from the light source 102 is split into the measurement light beam and the reference light beam by the coupler 104. The measurement light beam passes through an optical fiber and then is emitted into atmosphere. The emitted light beam is converged on the fundus Ef via the optical scanner 108 and other optical components of the measurement optical system 106. The light reflected from the fundus Ef travels a similar optical path and then returns to the optical fiber.

The optical scanner 108 scans the measurement light on the fundus in the X-Y direction (a transverse direction). The optical scanner 108 is disposed at a position substantially conjugate with a pupil. For example, two galvano mirrors constitute the optical scanner 108, and reflection angles of the galvano mirrors are arbitrarily adjusted by a drive mechanism 50.

Accordingly, a reflecting angle (a traveling angle) of the light beam emitted from the light source 102 changes so that the scanning can be performed on the fundus in any arbitrary direction. As a result, the imaging position in the transverse direction is changed. Examples of the optical scanner 108 are reflection mirrors (galvano mirror, polygonal mirror, and resonant scanner), and an acousto-optic device (AOM) which changes a travel direction of light (a deflection direction of light).

The reference optical system 110 generates the reference light to be synthesized with the measurement light reflected from the fundus. The reference optical system 110 may be a Michelson optical system or a Mach-Zehnder optical system. The reference optical system 110 is for example constituted of a reflective optical system (e.g., a reference mirror). The light output from the coupler 104 is reflected by the reflective optical system to return to the coupler 104 so that the light is guided to the detector 120. Another example of the reference optical system 110 is a transmission optical system (for example, an optical fiber), wherein the light output from the coupler 104 is not returned thereto but is transmitted through the transmission optical system to be guided to the detector 120.

The reference optical system 110 is configured to move the optical members present in a reference optical path to change a difference in optical path length between the measurement light and the reference light. For example, the reference mirror is moved in the direction of an optical axis. A device for changing the difference in optical path length may be provided in a measurement optical path of the measurement optical system 106.

The front observation optical system 200 includes an optical scanner which scans the measurement light emitted from the light source (for example, infrared light) two-dimensionally on the examinee's fundus, and a second light receiving element which receives the reflective light from the fundus through a confocal opening located at a position substantially conjugate with the fundus. The front observation optical system 200 is configured as a scanning laser ophthalmoscope (SLO).

As an alternative, the front observation optical system 200 may be configured as a fundus camera. The OCT optical system 100 can concurrently serve as an observation optical system 200, wherein the front image is captured based on the tomographic image data two-dimensionally obtained (for example, integrated image of three-dimensional tomographic images in the depth direction, an integrated value of spectral data at each position in X and Y directions).

The fixation target projecting unit (the presenting unit) 300 guides a line of sight of the eye E in a given direction. The fixation target projecting unit 300 has a visible light source which emits visible light and is arranged to change the fixation position of the examinee's eye two-dimensionally so that a site to be imaged is changed. The fixation target projecting unit 300 can be variously configured. For example, the fixation target projecting unit 300 is configured to adjust the fixation position by using LED lighting positions arranged in a matrix shape or adjust the fixation position by scanning the light from the light source using the optical scanner for lighting control of the light source. The projecting unit 300 may be an internal fixation lamp or an external fixation lamp.

<Measurement by Perimeter>

The perimeter 400 subjectively measures the visual field of the eye E based on a response result obtained when the fixation target is presented to the eye E. The perimeter 400 may be an active perimeter or a passive perimeter. The perimeter 400 is provided in a cabinet where the fundus imaging apparatus is housed or may be separately provided so that the measurement result thereby obtained can be independently used.

The active perimeter, while continuing to move the target, measures a point at which the examinee visually recognizes the target. The active perimeter draws an isopter by changing measurement conditions such as the size and/or brightness of the target, to measure the visual field.

The passive perimeter does not move the target but fixates the eye E at a position. Then, the passive perimeter irradiates a spot light on a plurality of stimulus points of the fundus Ef in turns so that a response result is obtained at each of the stimulus points. For example, the target is fixated and presented at a particular point in the visual field of the eye E, and the target is also presented at a different point. Then, a brightness differential threshold (visual sensitivity threshold) in a large area of the visual field is calculated from a result of visual recognition of the target.

<Description of Operation>

Figure 2:
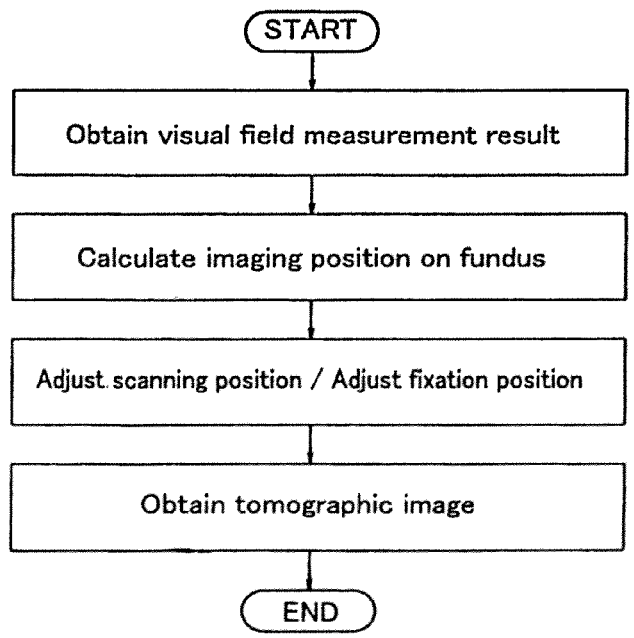
FIG. 2 is a flowchart to explain operations of the apparatus.

Hereinafter is described an operation of the apparatus having the above configurations. FIG. 2 is a flowchart to explain the operation of the apparatus. As a preliminary preparation before imaging, information of a patient (for example, ID number for identifying the patient, the patient's name, age, sex, and chief complaint, and remarks) is input. The control unit 70 reads the measurement result of the perimeter 400 for the input patient information.

<Setting Imaging Region by Using Measurement Result of Perimeter>

The perimeter 400 outputs information of the examined visual field of the fundus Ef (for example, information of the isopter and the visual sensitivity threshold) to the control unit 70. The control unit 70 obtains the measurement result when the visual field of the eye E was measured by the perimeter 400, and sets an imaging region (measurement region) of the fundus Ef to be imaged by the OCT optical system 100 based on the obtained measurement result.

The control unit 70 evaluate or assesses data of the obtained measurement result based on given criteria of evaluation. Then, the control unit 70 identifies any abnormal site of the fundus Ef based on a result of the evaluation. Thus, the control unit 70 analyzes the measurement result to identify the abnormal site, and the imaging region is set so that the identified abnormal site is tomographically imaged.

In place of the abnormal site, a normal site may be identified and set as the imaging region. In the case where an unusual indication is detected in the measurement result, a relevant site of the fundus may be set as the imaging region.

A measurement position of the perimeter 400 and an imaging position of the OCT optical system 100 are preferably tabulated so as to correspond with each other in advance. In the case where the measurement result of the perimeter 400 is associated with the fundus front image, the imaging position of the OCT optical system 100 and the fundus front image may be associated with each other.

The imaging region of the OCT optical system 100 can be viewed as a region of the fundus where the measurement light is irradiated, in which case a drive position of the optical scanner 108 and a measurement position of the perimeter may be associated with each other. In the case where the imaging region of the perimeter is larger than a scanning range of the measurement light by the optical scanner 108, the imaging region is set in consideration for the fixation position of the projecting unit 300 and the scanning range of the optical scanner 108.

Figure 3:
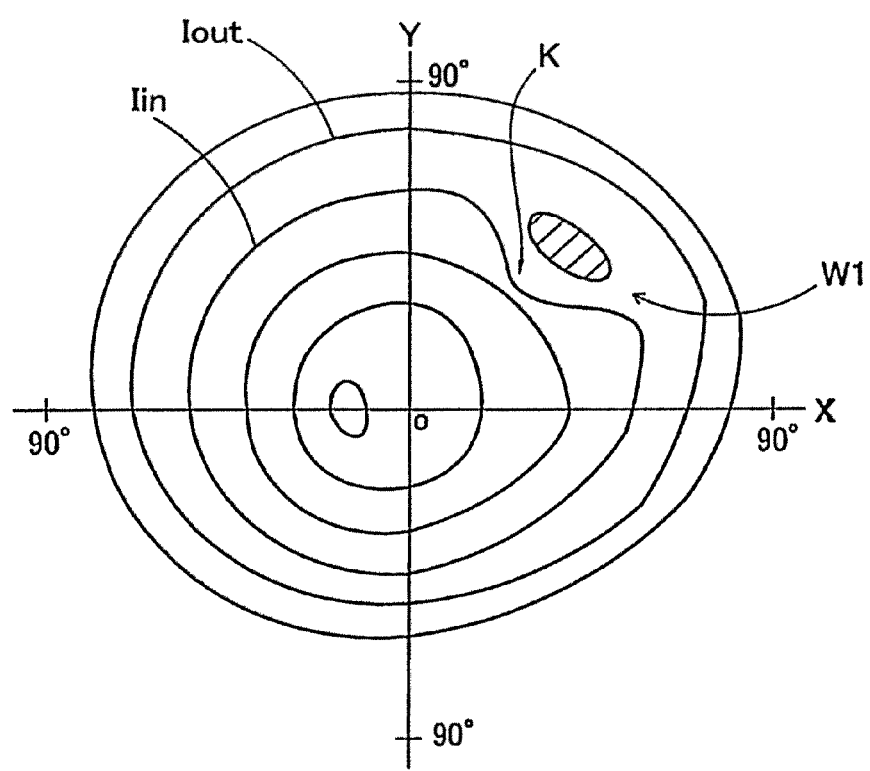
FIG. 3 is a diagram showing one example of isopter information of an eye obtained by a perimeter.
Figures 4, 5:
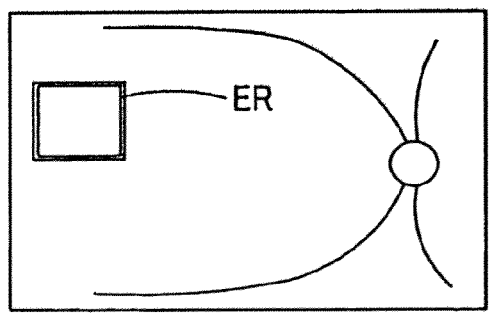
FIG. 4 is a diagram showing one example of calculating a measurement result from a passive perimeter.
FIG. 5 is a diagram showing an example to set an imaging position based on a result of measurement of a visual field.

As illustrated in FIGS. 3 and 4, for example, the control unit 70 obtains positional information of the abnormal site of the fundus from the obtained measurement result data and sets the imaging positional information on the fundus based on the positional information. The control unit 70 sets the imaging positional information so that the abnormal site is included in the imaging position.

FIG. 3 is a diagram illustrating an example of the isopter information of the eye E calculated by the perimeter. An inward dented portion of the isopter is called a dent K. The isopter having the dent K is called an isopter Iin, and an isopter on the outer side of the isopter Iin is called an isopter Iout. The dent K has a lower sensitivity than any other angular region centered on a visual field center O. Therefore, scotomas may present in a range from the dent K toward the isopter Iout on the outer side.

To calculate the imaging region using the active perimeter, the control unit 70, for example, obtains the isopter information (see FIG. 3) from the perimeter 400, and searches the dent K from a general shape of the isopter. When the dent K is identified, the control unit 70 identifies a region W1 between the dent K and the isopter Iout on the outer side of the dent K as an abnormal site and acquires the positional information of the identified abnormal site. The control unit 70 sets the imaging region of the OCT optical system 100 based on the positional information of the identified abnormal site.

To calculate the measurement result using the passive perimeter, for example, the control unit 70 obtains the visual sensitivity threshold information (see FIG. 4) from the perimeter 400 to search the measurement points where the respective thresholds fall below a range of tolerance (except optic papilla). When the points where the thresholds are below the level of tolerance are identified, a region including the points is identified as an abnormal site W2, and the positional information of the identified abnormal site is obtained. The control unit 70 sets the imaging region of the OCT optical system 100 based on the positional information of the identified abnormal site.

To set the imaging region, Aulthorn's classification modified by Greve (hereinafter, abbreviated to AG method) based on data of the passive visual field examination, which is a typical classification method for evaluating glaucomatous progression (pathological staging), may be employed. The measurement result is classified into a stage by the AG method. Therefore, the control unit 70 may set the imaging region depending on the stage defined by the AG method.

<Capturing Tomographic Image by OCT Optical System>

After the apparatus is aligned to the eye E, the apparatus starts to capture the tomographic image and the front image. The control unit 70 drives and controls the OCT optical system 100 and the front observation optical system 200 to obtain the OCT and SLO images per frame, and continually updates the OCT and SLO images to be displayed on the monitor 75.

The control unit 70 controls the operation of at least one of the optical scanner 108 and the projecting unit 300 to change the position on the fundus where the measurement light is irradiated. Then, the control unit 70 obtains the tomographic image of a part of the fundus set as the imaging region (for example, see ER illustrated in FIG. 5). The control unit 70, for example, obtains imaging conditions (lighting position of the fixation target, driving position of the optical scanner 108) of the apparatus necessary for the set imaging region based on a scannable range by the optical scanner 108 based on the measurement light and an amount of motion of the fundus Ef by the projecting unit 300.

In the case where any abnormal site is detected in a peripheral area of the fundus, for example, the control unit 70 sets the fixation position so that the abnormal site is included in the scannable range by the measurement light on the fundus Ef. Preferably, the control unit 70 sets the fixation position so that the abnormal site is located at the center of the scannable range. The scannable range is decided depending on driving ranges of the OCT optical system 100 and the optical scanner 108.

In the event of a visual field loss on a nose-side part of the fundus as illustrated in FIG. 4, the control unit 70 sets the fixation position in the projecting unit 300 on the nose-side part relative to the center so that a line of sight of the eye E is guided to the nose side. A deflection angle of the line of sight is determined by a distance from a measurement center (for example, central fovea) to a position of the visual field loss.

To obtain the tomographic image based on the perimeter 400, a scan pattern suitable for capturing the image of the abnormal site is preferably set. Further, such a scanning range that the whole abnormal site is included is preferably set. An example of the scan is raster scan performed to a rectangular region comparable to the size of the abnormal site. The fixation position is preferably set at a position appropriate for capturing the image of the abnormal site. A plurality of tomographic images may be obtained for one abnormal site and averaged so that an average image is obtained.

To obtain the tomographic image based on the measurement result of the perimeter 400, the control unit 70 may use an analysis result obtained by analyzing the measurement result of the perimeter 400 to start to obtain the tomographic image, or the control unit 70 may use the operation signals output from the mouse 76 as a trigger to start to obtain the tomographic image.

In the event that a plurality of abnormal sites are detected, for example, the control unit 70 obtains the tomographic image based on the perimeter 400 in such a scanning range that the plurality of abnormal sites are included, or the control unit 70 may set the scanning range comparable to each of the abnormal sites to obtain the tomographic images of the respective sites in turns.

The control unit 70 may output the measurement result by the perimeter 400 or displays the analysis result thereof on the monitor 75. In this case, the control unit 70 may continuously drives the OCT optical system 100 and the front observation optical system 200 to superimpose and display a graphic showing the measurement result (or the analysis result thereof) (for example, a marker appended to a part indicating the abnormal site) on a tomographic observation image and a front observation image, which are obtained in real time as moving images (for example, see a mark ER illustrated in FIG. 5). As a result, the examiner can confirm the abnormal site found by the perimeter 400 based on the observation images under examination.

The control unit 70 outputs the obtained tomographic images and the front images obtained at the same time as the tomographic images to the monitor 75 and also outputs a two-dimensional map relating to the measurement result by the perimeter 400 or the analysis result thereof to the monitor 75. The control unit 400 may superimpose and display a graphic showing the measurement result (or the analysis result thereof) (for example, a marker appended to a part indicating the abnormal site) on the tomographic observation image and the front observation image displayed on the monitor 75 (for example, see the mark ER illustrated in FIG. 5). As a result, the examiner can confirm the abnormal site found by the perimeter 400 based on the observation images under examination. The thus configured apparatus can set the measurement position at any desirable site based on the operation signals output by the operation unit such as a mouse.

<Tomographic Image Analysis>

Figure 8:
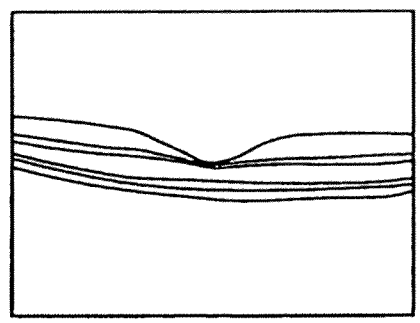
FIG. 8 is a diagram showing one example of a tomographic image.

When the tomographic image is obtained, the control unit 70 detects information of retinal layers in the tomographic images stored in the memory 72 by image processing and analyses a detection result of each layer based on predetermined conditions of image evaluation (criteria of evaluation) to determine whether or not the imaged site is normal. An evaluation result thereby obtained is displayed on the monitor 75 with the tomographic image. FIG. 8 is a diagram showing an example of the tomographic image displayed on the monitor 75.

The retinal layers are detected when the control unit 70 analyzes the luminance level of the tomographic image and detects a region comparable to certain retinal layers (for example, retinal surface layer and pigmented layer). To decide which part is to be imaged, for example, thicknesses and shapes of the layers and the size of a predetermined site are evaluated. A database in which inter-layer intervals and shapes and sizes of predetermined sites in a normal eye are stored is used as basic data of the image evaluation conditions.

As a result of the operation described so far, the tomographic images based on the measurement result of the perimeter 400 can be smoothly obtained. More specifically, a part of the fundus determined as being abnormal in the visual field examination, for example, can be smoothly tomographically imaged. The abnormal site related with the visual field can be reliably tomographically imaged, which ensures that any change in the examinee's eye condition is detected. This helps to decide appropriate medicinal approaches (for example, early detection of glaucoma).

<Comparison of Perimeter and OCT Measurement Results>

Then, the control unit 70 displays the obtained tomographic image and the analysis result thereof (for example, thickness map, comparison to normal eye database) and the measurement result of the perimeter 400 on the monitor 75.

Figure 6:
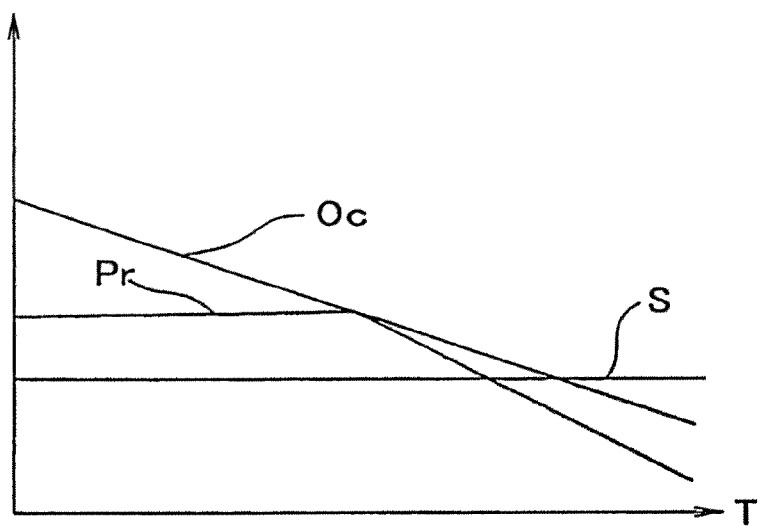
FIG. 6 is a graph showing variations with time of a parameter obtained by tomographic image analysis and a parameter obtained by a perimeter.

FIG. 6 is a graph showing variations with time of a parameter obtained by analyzing the tomographic image and a parameter obtained by the perimeter 400. A vertical axis represents values of the parameters, and a lateral axis represents time. The graph illustrated in FIG. 6 can be drawn when the examination by the perimeter 400 and the examination by the fundus imaging apparatus 100 are performed at regular intervals.

Examples of a parameter Pr of the perimeter are; an MD value (Humphrey perimeter), an average value of visual sensitivity threshold values, PSD (pattern standard deviation), CPSD (correction pattern standard deviation), and SF (short-term fluctuation). Examples of a parameter Oc of the fundus imaging apparatus are; a C/D ratio (cup/disc ratio), a retinal thickness, and an area where the retinal thickness falls below normal values.

For example, the control unit 70 obtains examination dates and times and parameter values stored in the memory 72 and displays variations of the parameters from the first medical visit. The control unit 70 may display a threshold value H for each of the parameters (see FIG. 6) as a target value based on which any abnormality is identified.

Accordingly, deteriorations of the visual field detected by the perimeter 400 and the fundus imaging apparatus can be both confirmed on the same graph. Therefore, the examiner can easily identify any pathological problem.

The imaging position setting unit configured to set the imaging position on the fundus may be provided in a cabinet separately from the cabinet of the OCT device. In this case, the imaging position setting unit outputs the set imaging positional data to the OCT device. The OCT device captures the tomographic image based on the imaging positional data. The imaging position setting unit may be provided on the side of the perimeter.

<Extensive Imaging and Imaging of Abnormal Site>

The control unit 70 may obtain an extensive tomographic image at a standard fixation position in vicinity of an optical axis (for example, the optical axis of an objective lens) (a position where macula (a yellow spot) and optic papilla are imaged in a balanced manner) as a standard image as well as the tomographic image of the abnormal site identified based on the measurement result of the perimeter 400. For example, the control unit 70 sets such a region that is narrower than the region of the extensive tomographic image and includes the whole abnormal site as a second imaging position.

Figure 7:
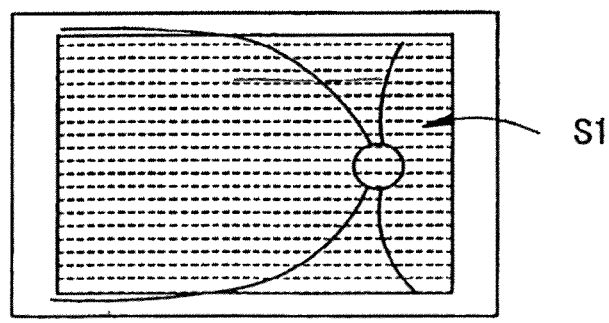
FIG. 7 is a diagram showing a case of scanning on a large area of a fundus.

For example, the control unit 70 scans the measurement light two-dimensionally on a large area of the fundus by driving the optical scanner 108 to obtain an extensive tomographic image of the fundus (a first tomographic image) (for example, see a hatching area S1 in FIG. 7). At the time, it is preferable to set a scanning range so that the macular and the optic papilla of the fundus are included in the imaging range (for example, a rectangular region of 9 mm high×9 mm wide or rectangular region of 12 mm high×12 mm wide). Examples of a scan pattern are a plurality of line scans, and raster scan. As a result, a plurality of tomographic images constituting extensive tomographic information of the fundus can be captured.

Next, the control unit 70 obtains the tomographic image based on the measurement result of the perimeter 400. In the case where the abnormal site is detected outside the scanning range for obtaining the extensive tomographic image, the control unit 70 drives the optical scanner 108 and the projecting unit 300 to obtain the tomographic image of the detected abnormal site, so that a second tomographic image is obtained.

In the case where the abnormal site is detected in a part of the scanning range for obtaining the extensive tomographic image, the control unit 70 sets a scanning range comparable to the size of the detected abnormal site and drives the optical scanner 108 in the set scanning rage, so that the second tomographic image is obtained.

Then, an analysis result of the standard image and the measurement result by the perimeter 400 are compared to each other. In the case where any abnormal site is newly found in the standard image, the standard image can be compared to the measurement result by the perimeter 400. For example, correlativity between the tomographic image analysis result and the measurement result by the perimeter 400 is calculated.

When any site determined as having a poor sensitivity by the perimeter 400 is tomographically imaged in addition to capturing the standard image, an integrative examination result, in which the tomographic image analysis result and the measurement result by the perimeter are combined, can be obtained. As a result, any change of the examinee's fundus condition can be reliably known.

According to the aforementioned description, the imaging position of the fundus is automatically set based on the measurement result by the perimeter 400, however, the imaging position is not necessarily automatically set. For example, a visual field map showing the measurement result by the perimeter 400 (see FIGS. 3 and 4) may be displayed on the monitor 75 to set the imaging position on the map.

At that time, the examiner selects a scanning pattern and also selects a predetermined position on the visual field map by manipulating such an operation input part as a mouse. For example, a rectangular scanning pattern is electronically displayed on the monitor 75, and the imaging position is set in such a manner that the abnormal site on the visual field map is encompassed by the displayed scanning pattern.

<Matching Between Measurement Position by Perimeter 400 and Tomographic Image Capturing Position>

When the visual field is to be measured by the perimeter 400, an index pattern is projected with a macula portion (or preferably central fovea) as a measurement center. The control unit 70 may correct the irradiation position so that the measurement position on the fundus by the perimeter 400 and the imaging position by the OCT optical system 100 are consistent with each other. The control unit 70 drives at least one of the OCT optical system 100 and the front observation optical system 200 to receive the light reflected from the fundus so that the fundus image is captured. The control unit 70 detects the macular portion in the fundus image by image processing to detect any motion of the fundus. The control unit 70 corrects the irradiation position based on a detection result thus obtained.

Below is given an example. The control unit 70 identifies the macula portion in the fundus image by image processing and obtains the tomographic image with the identified macula portion as a center of the image. When the macula portion is identified from the fundus image, for example, the macula portion can be extracted based on its position, luminance value, and shape in the tomographic image. The macula portion has a circular shape and also has a lower luminance value than its peripheral portion. The image processing are performed so that an image region that matches the characteristics of the macula portion is extracted. The central fovea has a lowest luminance level in the macula portion, therefore, the image processing are performed so that an image region that matches the characteristics of the central fovea is extracted.

Below is described an example of the operation. The control unit 70 obtains the positional information of the abnormal site (for example, a distance from the measurement center) based on a measurement center in the measurement result by the perimeter 400. Then, the control unit 70 extracts the macula portion from a first front image captured by the front observation optical system 200. The control unit 70 sets an imaging region centered on a position where the macula portion was extracted based on the positional information of the abnormal site in the measurement result by the perimeter 400. For example, a distance from the measurement center to the abnormal site is calculated, and a region away by the calculated distance from the macula portion in the first front image is set as the imaging region. In the operation example, there is a correspondence relationship between the imaging positions of the front observation optical system 200 and the OCT optical system 100.

Next, the control unit 70 calculates a positional shift (deviation) between the first front image and the front image captured continuously by image processing to correct the imaging position of the tomographic image whenever necessary so that any positional shift is cancelled. In this case, for example, the scanning position of the optical scanner 108 is corrected. Accordingly, the tomographic image based on the measurement center of the perimeter 400 can be obtained irrespective of any motion of the fundus, and the measurement result of the perimeter 400 and the tomographic image analysis result can be thereby accurately compared to each other. In place of comparing the fundus images, the control unit 70 may detect the position of the macula portion in the captured front image to correct the imaging position based on the macula portion.

In place of the technical configuration described so far, the front image and the measurement result of the perimeter 400 may be associated with each other to detect any positional shift between the front image thus associated with the measurement result and the continuously captured front image, so that the imaging position is corrected.

<Perimeter 400 and Fundus Imaging Apparatus>

According to the aforementioned description, the tomographic image is captured by the fundus imaging apparatus based on the measurement result of the perimeter 400. The measurement conditions of the perimeter 400 may be set based on an analysis result obtained by the fundus imaging apparatus.

For example, the control unit 70 obtains in advance the extensive tomographic image as described above. Then, the control unit 70 calculates thicknesses of retinal layers (for example, retinal surface layer and pigmented layer) of the tomographic image. The control unit 70 two-dimensionally calculates any position where the layer thicknesses are beyond a predetermined range and identifies the position as the abnormal site. A comparison result of the layer thicknesses between the examinee's eye and a normal eye in X-Y directions may be used. When the layer thicknesses are thus used in the analysis, a total value of the thicknesses of the respective layers may be used.

The perimeter 400 measures the visual field of a part of the fundus identified as the abnormal site. For example, the perimeter 400 sets the part identified as the abnormal site as a measurement point and projects an indicator for the measurement point (active index, passive index).

<Obtaining Tomographic Image based on Fluoroscopic Image>

In the aforementioned description, the optical coherence tomography is controlled based on the examination data of the perimeter. Hereinafter, a method of controlling the optical coherence tomography based on other examination data is disclosed.

The control unit 70 may analyze a contrast-enhanced fluoroscopic image (fluorescent images obtained by FAG (fluorescein fundus angiography) and ICG (indocyanine green imaging)) captured by the fundus camera or SLO, determines whether there is any abnormal site and positionally identify the abnormal site, if any, and then adjust the imaging position of the OCT optical system 100 to obtain the tomographic image of the abnormal site. The fluorescent image and the imaging position of the OCT optical system 100 preferably have a correspondence relationship therebetween.

In the front image, any abnormal site is presented in the form of a luminance variation (bright/dark). In the fluorescein imaging, a contrast agent transfers through blood vessels of the fundus in a normal eye, however, the contrast agent leaks on the fundus in an eye with abnormality such as age-related macular degeneration. Therefore, the abnormal site is identified by specifying a site where the fluorescent agent is leaking.

The control unit 70 identifies the fluorescent site in the obtained fundus image by image processing to evaluate whether the fluorescent site is abnormal. For example, the control unit 70 detects an image region having a higher luminance than a given luminance level previously set to extract the fluorescent site by image processing. Then, the control unit 70 identifies an abnormal site (K) from the size and shape of the fluorescent site.

The fluorescent site in a blood vessel has a thin and very unique shape comparable to the blood vessel. The leakage site has a relatively large size and a shape different from that of the blood vessel. This information is useful to discriminate the leakage site from the blood vessel.

The control unit 70 may compare an ordinary front image (for example, color fundus image, infrared fundus image) of the fundus Ef to the fluorescent front image to identify the leakage site. The control unit 70 may extract a blood vessel region of the ordinary front image of the fundus by image processing and checks whether the extracted blood vessel region matches with the fluorescent front image and determines the unmatched fluorescent site as being abnormal.

The tomographic image can be obtained for the site determined as being abnormal based on the fluorescent image in a manner similar to the tomographic image captured based on the measurement result of the perimeter 400, which is, therefore, not described again.

<Perimeter Control Method Based on Optical Coherence Tomography>

Figure 9:
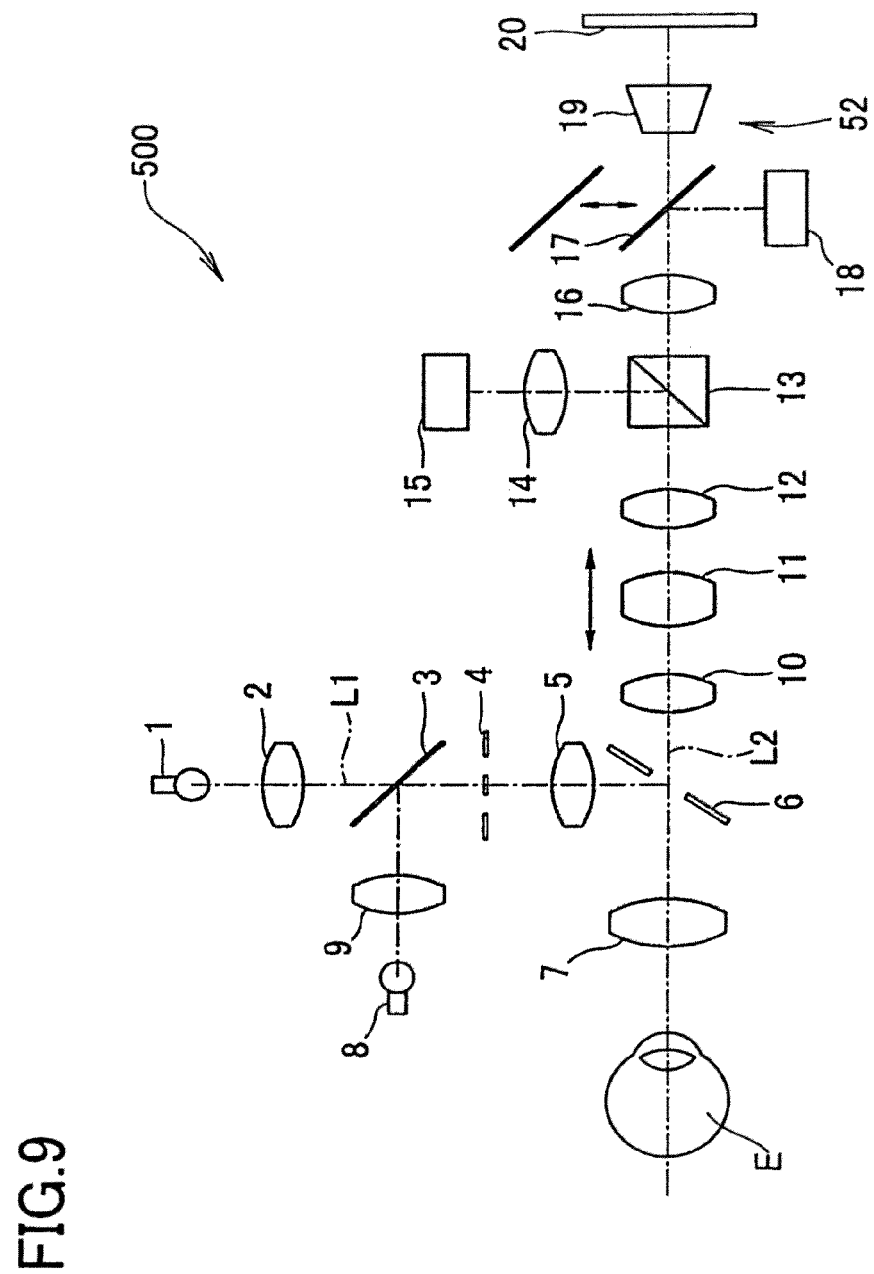
FIG. 9 is a configuration view of an optical system in a fundus examination apparatus according to a second embodiment.
Figure 10:
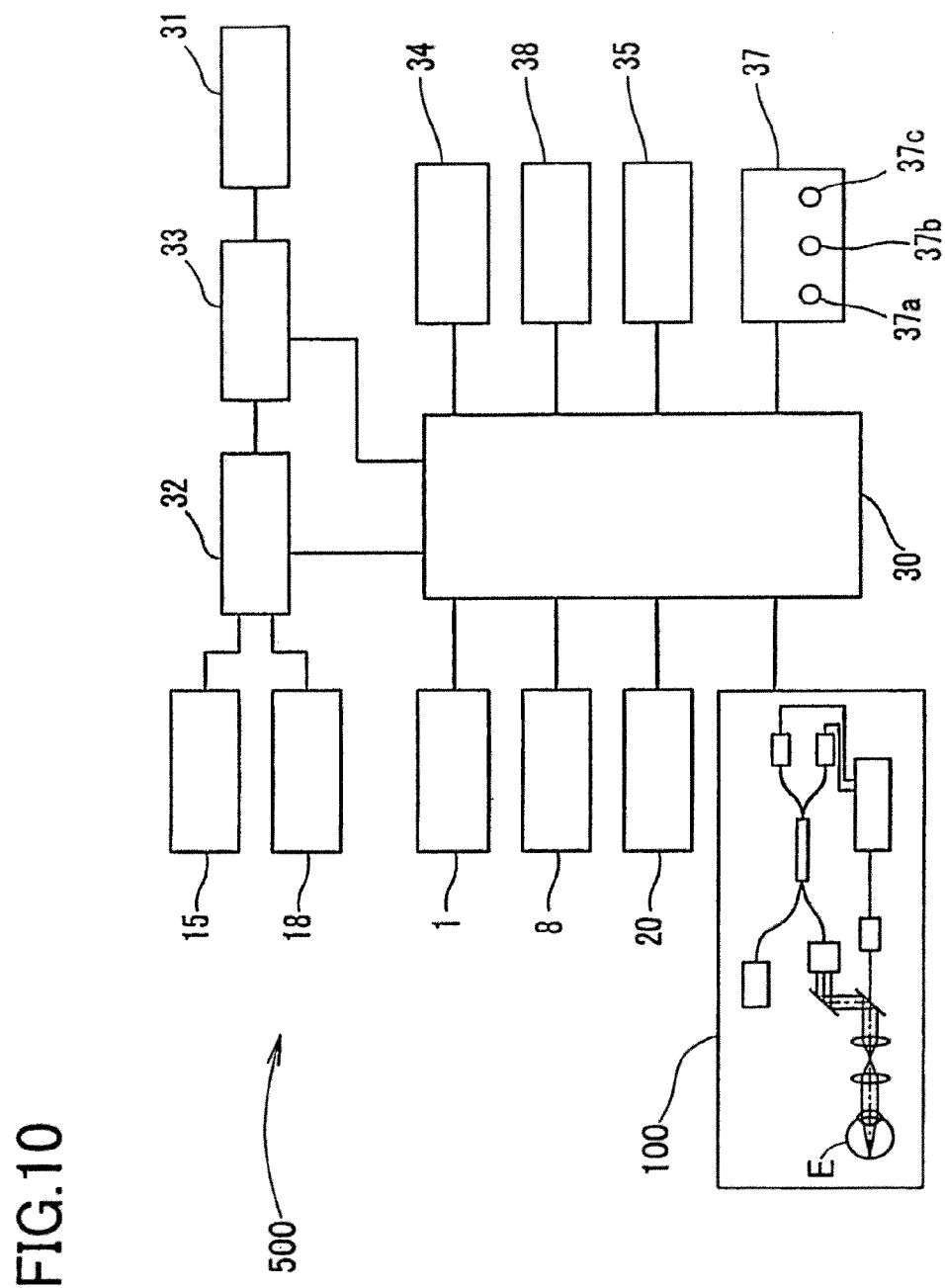
FIG. 10 is a block diagram of a control system.

A second embodiment of the present invention will be described below referring to the accompanied drawings. FIG. 9 is an illustration of a structure of an optical system in a fundus examination apparatus according to the present embodiment. FIG. 10 is a block diagram of a control system.

The structure of the fundus examination apparatus (perimeter according to the present embodiment) is schematically described. In a perimeter 500, conditions for presenting stimulus targets are set. The perimeter 500 presents an examination target to an examinee's eye E and also measures a response by the examiner to thereby measure a visual field of the eye E. The perimeter 500 is provided with a target presenting optical system 52 which presents stimulus targets in the visual field of the eye E.

A control unit 30 provided in the apparatus obtains an analysis result data based on a fundus image captured by a fundus imaging apparatus (for example, the optical coherence tomography device (OCT device) 100). The control unit 30 sets a region where the stimulus targets are presented and also sets a plurality of measurement points in the target presenting region based on the obtained analysis result data. The control unit 30 presents the stimulus targets at the set measurement points in turns by controlling the operation of the target presenting optical system 52 to examine the visual field.

Hereinafter, the structure of the perimeter is described in detail. In FIG. 9, a reference symbol E denotes an examinee's eye. A light source 1 emits infrared light. A halogen lamp and an infrared transmitting filter may be used to emit an infrared beam. The infrared beam emitted from the light source 1 is irradiated on a ring slit 4 through a condenser lens 2 and a cold mirror 3 provided on an optical axis L1. The light beam from the ring slit 4 passes through a relay lens 5 and forms an intermediate image near the opening of a perforated mirror 6. The light beam from the ring slit 4 is also reflected by a peripheral surface of the perforated mirror 6 provided on an optical axis L2. The ring-slit light reflected by the perforated mirror 6 forms an image near the pupil of the examinee's eye E through an objective lens 7 and then diffuses to uniformly irradiate the fundus of the examinee's eye. The cold mirror 3 has a property of reflecting visible light and transmitting therethrough infrared light. Flash light emitted from an imaging light source 8 including a xenon flash lamp having passed through a condenser lens 9 is reflected by the cold mirror 3 and then passes through the ring slit 4, relay lens 5, perforated mirror 6, and objective lens 7 to be finally irradiated on the fundus of the examinee's eye E. These components constitute an illumination optical system.

The light beam (infrared beam) reflected from the fundus of the examinee's eye E having transmitted through the objective lens 7, perforated mirror 6, and lenses 10, 11, and 12 provided on the optical axis L2 is reflected by a beam splitter 13 having a property of reflecting infrared light and transmitting therethrough visible light, and then guided to a lens 14. The light beam guided to the lens 14 finally forms an image on a light receiving surface of an observation CCD camera 15 having sensitivity to an infrared region. The opening of the perforated mirror 6 located at a position conjugate with the pupil of the examinee's eye constitutes an imaging diaphragm. The lens 11 is a focusing lens that can be driven in the direction of the optical axis. When the position of the lens 11 on the optical axis L2 is changed, the fundus of the examinee's eye E and the light receiving surface of the camera 15 can have a conjugate relationship therebetween. The devices or components from the objective lens 7 through the camera 15 constitute an infrared imaging optical system also serving as an observation optical system.

The devices or components from the objective lens 7 through the beam splitter 13 of the observation optical system are also used by the imaging optical system using the visible light. The visible light reflected from the fundus and having transmitted through the beam splitter 13 is reflected by a mirror 17 via a lens 16 and then enters an imaging CCD camera 18 having sensitivity to a visible range to form a fundus image on the light receiving surface of the CCD camera 18. The light receiving surface of the camera 15 is located at such a position optically conjugate with the light receiving surface of the camera 18 and the fundus of the examinee's eye. An imaging field angle is 45 degrees in visible imaging and infrared imaging respectively.

The devices or components from the objective lens 7 through the lens 16 of the imaging optical system are also used by the target presenting optical system 52 for subjectively measuring a visual field. The target presenting optical system 52 includes a reducing lens 19 and an LCD display 20 which displays a target for measuring the visual field. The reducing lens 19 is used to project a whole target presenting region of the LCD display 20 on the examinee's eye E. During the measurement of the visual field (when the target is being presented), the mirror 17 is moved out of the optical path. The target displayed on the LCD display 20 is projected on the fundus of the examinee's eye E by way of the reducing lens 19, lens 16, beam splitter 13, lenses 10 to 12, perforated mirror 6, and objective lens 7. At the center of the LCD display 20 (optical axis L2), a cross-shaped fixation target is formed as a fixation target for the examinee's eye. The presenting positions, luminance levels and sizes of the examination targets for measuring the visual field (stimulus targets) can be variously changed.

Referring to FIG. 10, a control unit 30 drives the whole system of the fundus examination apparatus. The observation light source 1, the imaging light source 8, the LCD display 20 an image processor 32, an image changer 33, a memory 34, and a response button 35 are connected to the control unit 30. The response button 35 is used when the examinee can visually recognize the presented target during the measurement of the visual field. To the control unit 30, further, an imaging button 37a, a mode change button 37b for switching to and from, for example, a fundus imaging mode and a visual field measurement mode, and a control unit 37 provided with, for example, a start button 37c for starting the visual field measurement are also connected.

The image processor 32 performs image processing to images captured by the camera 18. The image processor 32 can also perform image processing to images obtained by the camera 15. The image changer 33 changes an image to be displayed on the monitor 31 to a moving observation image captured by the camera 15 or a still image captured by the camera 18. The memory 34 stores therein the images captured by the cameras 15 and 18 and information of the examinee's responses obtained during the visual field measurement. Further, the control unit 30 performs an arithmetic operation during the subjective measurement of the visual field.

<Measurement by OCT>

The OCT device 100 irradiates measurement light on a fundus Ef and detects a state of coherence between the measurement light reflected from the fundus and reference light to capture a tomographic image of the fundus. The OCT device 100 includes an optical coherence system configured to split the light beam emitted from the light source into the measurement light and first reference light and then guide the measurement light to the fundus and the reference light to a reference optical system and thereafter receive coherent light obtained by combining the measurement light reflected from the fundus with the reference light. On a measurement optical path of the optical coherence system, there is provided an optical scanner which makes the measurement light scan the fundus.

<Analysis by OCT>

Figure 11:
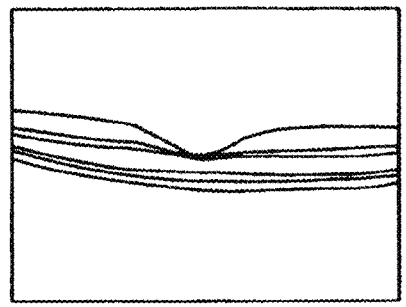
FIG. 11 is a diagram showing an example of a tomographic image obtained by an OCT device.

FIG. 11 is a diagram showing an example of the tomographic image obtained by the OCT device 100. The OCT device 100 has an image analyzer to detect information of layers of the fundus in the obtained tomographic image by image processing and analyze a detection result of each of the layers based on predetermined image evaluation conditions (criteria of evaluation) to evaluate whether an imaged site is normal or not. The OCT device 100 obtains an analysis result based on a resulting evaluation result. The analysis result is stored in the memory of the OCT device 100 or an external memory (for example, in a memory of a personal computer or a server) with the tomographic image.

To detect the layers, for example, the luminance level of the tomographic image is detected, and a boundary between the retinal layers (for example, a retinal surface layer and a pigmented layer) is extracted by image processing. Then, an inter-layer interval is measured so that layer thicknesses are measured.

To evaluate the tomographic image, for example, the thickness or shape of each layer or the size of a given site (for example, optic papilla, macula) is evaluated. A normal eye database in which inter-layer intervals, shapes and sizes of predetermined sites in a normal eye are stored is used as basic data of the image evaluation conditions. The normal eye database is stored in the memory.

For example, the OCT device 100 measures the layer thicknesses at positions in the transverse direction to evaluate whether a measurement result is in a predetermined range in the normal eye database (a normal range equivalent to measured values of a normal eye). The OCT device 100 determines any site where the layer thicknesses are included in the normal range as an unaffected site, while determining any site where the layer thicknesses are beyond the predetermined range as an affected site. Thus, an abnormal site in the tomographic image is identified.

Figure 12:
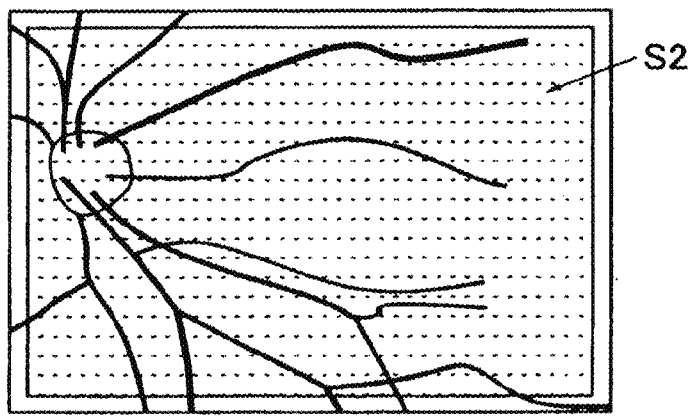
FIG. 12 is an explanatory view showing an example of scanning a large area of a fundus.

An extensive tomographic image captured by making the measurement light two-dimensionally scan a large area of the fundus (for example, see a hatching area S2 illustrated in FIG. 12) may also be used as the image to be analyzed. In this case, it is preferable to set a scanning range so that the macula and optic papilla of the fundus are included in the imaging range (for example, a rectangular region of 9 mm high×9 mm wide or a rectangular region of 12 mm high×12 mm wide). Examples of a scan pattern are a plurality of line scans, and raster scan. As a result, a plurality of tomographic images constituting extensive tomographic information of the fundus can be obtained.

The OCT device 100 calculates the thicknesses of the retinal layers (for example, a retinal surface layer and a pigmented layer) in the tomographic images. Then, the OCT device 100 two-dimensionally obtains any positions where the layer thicknesses are beyond a predetermined range. A comparison result of the layer thicknesses between the examinee's eye and a normal eye in X-Y directions may be used. In the analysis using the layer thicknesses, naturally, a total value of the thicknesses of the respective layers may be used.

Figure 13:
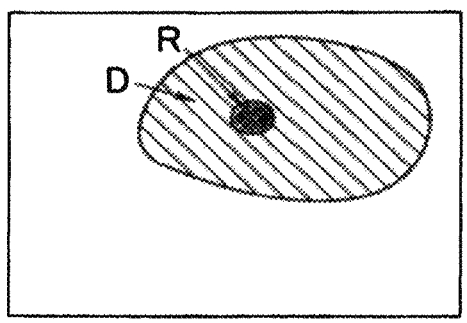
FIG. 13 is a diagram showing an analysis result of the tomographic image, which is an example of a thickness map when layer thicknesses are two-dimensionally measured.

FIG. 13 is a diagram showing an analysis result of the tomographic image, which is an example of a thickness map when the layer thicknesses are two-dimensionally measured. A hatching area R represents a part where the layer thicknesses are beyond a first predetermined range set for identifying any abnormal site. This site is displayed in, for example, red. A hatching area D represents a part where the layer thicknesses are beyond a second predetermined range set for identifying a high-risk site (an intermediate level between a normal condition and an abnormal condition). This site is displayed in, for example, yellow.

To evaluate a glaucomatous progression in the analysis, thicknesses of a retinal nerve fiber layer and a gangliocyte layer are preferably measured and compared to the normal eye database to identify any abnormal site. A total thickness dimension including the thicknesses of the retinal nerve fiber layer, gangliocyte layer, and intimal layer may be measured and analyzed.

An analysis result based on the tomographic image obtained by the OCT device 100 includes, for example, measurement information based on the tomographic image, evaluation result based on the measurement information, information of a disorder based on the tomographic image, and positional information of any abnormal site on the fundus.

The measurement information includes, for example, layer thicknesses, shapes, and size of a particular site. The evaluation result includes, for example, a comparison result obtained by comparing the measurement result of the tomographic image to the normal eye database (for example, a result obtained by comparing the layer thickness information of the fundus tomographic image to the normal eye database), and map images based on the comparison result. The disorder information includes, for example, the name of disorder of the examinee, and a stage of progression of a particular disorder.

The analysis result may be a result obtained when the examiner identifies an abnormal site based on the tomographic image in place of the analysis by image processing.

The analysis result may also be a result associated with the fundus front image obtained by a front fundus imaging device (for example, a fundus camera, an SLO (scanning laser ophthalmoscope) attached to the OCT device 100.

<Description of Operation>

The operation of the apparatus having the above configurations is described below. Briefly describing the operation, the perimeter of the present embodiment generates a visual field examination pattern (for example, a target presenting position, a target luminance level, etc.) based on a fundus abnormality information obtained by the OCT device 100 capable of morphologically observing the retina. The perimeter performs an examination based on the generated examination pattern to check in details the visual field associated with a particular abnormal site.

Figure 14:
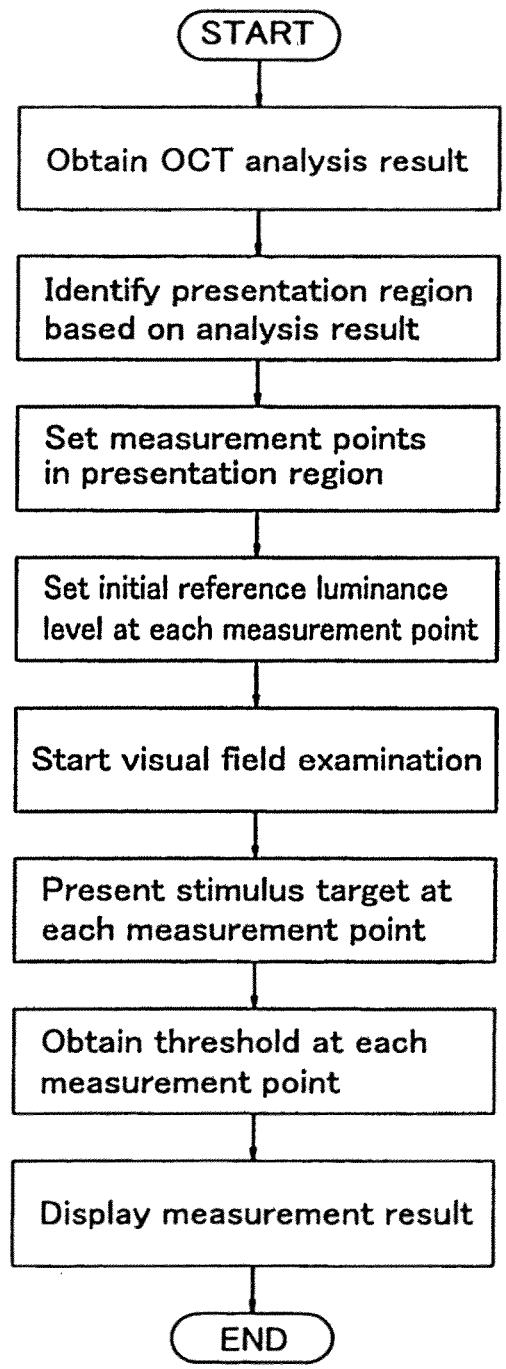
FIG. 14 is a flowchart to explain an example of operation of the apparatus.

FIG. 14 is a flowchart to explain an example of the operation of the apparatus. As a preliminary preparation before imaging, information of a patient (for example, ID number for identifying the patient, the patient's name, age, sex, and chief complaint, and remarks) is input. The control unit 30 reads the analysis result of the OCT device 100 corresponding to the input patient information and displays the analysis result on the monitor 31. For example, the analysis result is input from the OCT device 100 to the perimeter via a LAN cable. The analysis result may be input to the perimeter from a server or the like in which the tomographic images and analysis results obtained by the OCT device 100 are stored.

The control unit 30 processes data of the obtained analysis result based on at least one criterion of evaluation to obtain positional information of the abnormal site of the fundus. The control unit 30 sets a region where stimulus targets are to be presented based on the obtained positional information. The control unit 30 sets a plurality of measurement points in the set target presenting region. The control unit 30 obtains data of a degree of abnormality included in the analysis result data and changes an initial reference luminance level at each of the measurement points in a stepwise fashion depending on the degree of abnormality.

Figure 15:
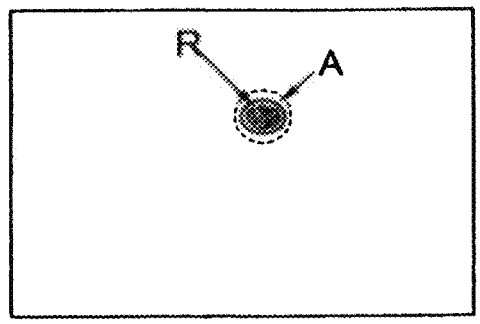
FIG. 15 is an explanatory view to explain an example of setting a presenting region of a stimulus target based on an analysis result data.
Figure 16:
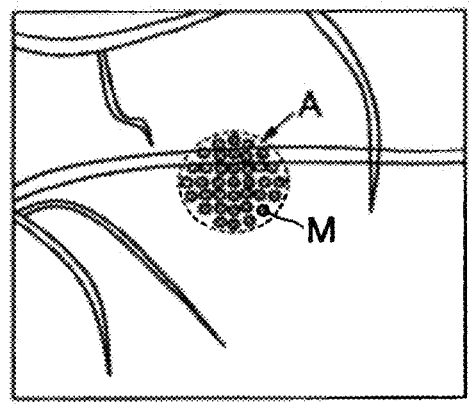
FIG. 16 is a diagram to explain an example of setting a plurality of measurement points in the presenting region.

For example, the control unit 30 obtains positional information of a site in which the layer thicknesses are beyond a preset range of a normal eye and sets the region where the stimulus targets are to be presented based on the positional information. When an analysis result illustrated in FIG. 13 is obtained, the control unit 30 obtains a positional information of a part determined as an abnormal site (the hatching area R) and sets a stimulus target presenting region A so that the abnormal site is included in a measurable range (see FIG. 15). The control unit 30 sets a plurality of measurement points M (black circles) at predetermined intervals in the presenting region A so that detail information of the visual field in the abnormal site is obtained (see FIG. 16). The initial reference luminance level at each of the measurement points is changed depending on an amount of deviation of the layer thicknesses from a range of tolerance (for example, the luminance level is increased as the amount of deviation is larger). In the event of a plurality of abnormal sites, positions to be examined by the perimeter on the fundus are set based on the positional information so as to include the plurality of abnormal sites.

The analysis result of the OCT device 100 and the measurement points in the visual field examination are configured beforehand to have a correspondence relationship therebetween, and the correspondence relationship is stored in the memory 34. For example, the target presenting positions of the perimeter and the measurement positions of the OCT device 100 (for example, a measurement light scanning position, a fixation position) are stored so as to correspond to each other. Because an aberration of the optical system provided in the OCT device may result in distorting both the tomographic image and the analysis result, the target presenting positions correspond to the measurement positions after such a distortion is corrected.

Then, the control unit 30 controls the display 20 to present the stimulus targets in turns at the measurement points in the set presenting region. The control unit 30 starts the visual field measurement with the set initial reference luminance level at each of the measurement points displayed on the display 20.

Receiving a response signal of the response button 35 from the examinee, the luminance level at the relevant measurement point is sequentially decreased by a given luminance (4 db) when the target is thereafter presented again. Receiving no response from the examinee, the luminance level is increased by a predetermined luminance level (made brighter). Before and after receiving or not receiving the visibility response, the luminance level is increased or decreased by 1 db, and the darkest luminance level that can be visually recognized is ultimately set as a threshold at the measurement point. This threshold setting is performed at each of the measurement points in the presenting region A.

Figure 17:
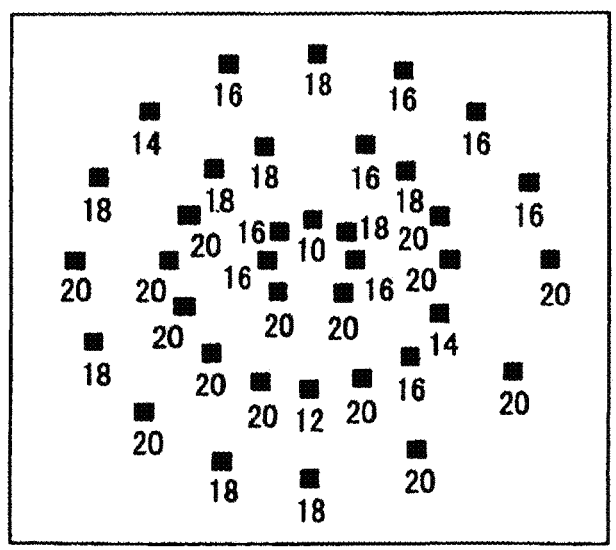
FIG. 17 is a diagram showing an example of a result of visual field measurement.

When the visual field measurement is completed at all of the set measurement points, the threshold information of each measurement point is displayed on the monitor 31 as illustrated in FIG. 17. This threshold information, when displayed, may be superimposed on the fundus image captured by the camera 18 stored in the memory 34. Because the analysis result is associated with each of the measurement points in the visual field examination, the measurement result, when displayed, may be superimposed on the analysis result such as a layer thickness map.

With the above configuration, a subjective visual field examination result can be obtained in any region identified as an abnormal site by the OCT device 100. Thus, the subjective measurement can be smoothly confirmed for any region identified as being morphologically abnormal based on the tomographic image. Therefore, the disorder of any affected site can be smoothly measured.

Further, a database (for example, normal eye database) for identifying a fundus disorder (fundus abnormality) is used to analyze the tomographic image, and a site undergoing visual disturbance assumed from the identified fundus disorder is examined based on a target examination pattern suitable for the fundus disorder. This provides very useful information for diagnosis.

In place of the abnormal site, a normal site may be identified and set as the presenting region. In the case where an unusual result is obtained in the analysis result, a site relevant thereto may be set as the presenting region.

A presenting condition setting unit which sets conditions for presenting the stimulus targets may be provided separately from the perimeter. In this case, the presenting condition setting unit outputs data of the set presenting conditions to the perimeter. The perimeter examines the visual field based on the data of the presenting conditions. The presenting condition setting unit may be provided in the OCT device 100.

The presenting region A may be set so that the sites determined as the abnormal site and the high-risk site (hatching areas R and D) are included in the measurable range. The presenting region may be set for each of the abnormal site and the high-risk site so that the targets are presented in different steps. The presenting region A formed by the plurality of measurement points may have a circular shape, a rectangular shape, or any shape equivalent to a region of the abnormal site.

The number of the measurement points and intervals between the measurement points may be changed in a stepwise fashion depending on a degree of abnormality in the analysis result. For example, the intervals between the measurement points are changed depending on an amount of deviation of the layer thicknesses from a normal range of the normal eye database. As a result, the visual field of any abnormal site is more smoothly measured.

In the analysis result based on the tomographic image, whether the measurement result at each position indicates an abnormal or normal condition is color-displayed in a stepwise fashion in a two-dimensional map of the layer thicknesses of the fundus. The control unit 30 therefore may set the presenting region based on the color information of the two-dimensional map, in which case a relationship between the color information and the degree of abnormality is obtained in advance. The control unit 30 may display the two-dimensional map on the monitor 31 so that the examiner can set the target presenting positions of the perimeter on the two-dimensional map, in which case an operation unit for selecting the target presenting positions on the two-dimensional map is provided. The control unit 30 may display the fundus image (fundus front image) captured by at least one of the camera 15 and the camera 18 on the monitor 31 and further display the two-dimensional map superimposed on the fundus image. Accordingly, the target presenting positions can be set referring to the two-dimensional map.

In the two-dimensional map, for example, the normal site is displayed in blue, the high-risk site is displayed in yellow, and the abnormal site is displayed in red. Therefore, the control unit 30 may set the red region as the presenting region A or may set the red region as a first presenting region and the yellow region as a second presenting region. The first presenting region and the second presenting region may have different initial reference luminance levels (for example, first presenting region: high luminance, second presenting region: low luminance).

In the above explanation, the visual field examination result when examined by the perimeter based on a visual field examination pattern and the OCT analysis result based on the tomographic image may be stored to consequently build a database in which the visual field examination result data and the OCT analysis result data are associated with each other. Such a database provides a correlative relation between the fundus abnormality information identified by the OCT device 100 and the fundus abnormality information by the perimeter.

For example, the threshold information of the measurement points and the layer thickness information of the fundus at each of the measurement points are associated with each other so as to build a database pertinent to the correlative relation between the threshold values and the layer thickness. Such a database helps to identify any relationship between the visual field condition of the eye E and the tomographic image.

The control unit 30 may obtain the target presenting conditions for the obtained analysis result data from a database in which the visual field examination result and the OCT analysis result are stored. In this case, a pattern database in which the visual field examination pattern for the analysis result of the tomographic image is stored may be built.

For example, an estimated threshold value for the layer thicknesses of the eye E is calculated referring to the database pertinent to the correlative relation between the threshold values and the layer thicknesses, and a luminance level close to the estimated threshold value is set as the initial reference luminance level. This enables smoother visual field examination. The visual field examination pattern for the obtained layer thickness information may be obtained from the pattern database.

The abnormal region identified by analyzing the tomographic image and the abnormal region identified by the perimeter are not always consistent with each other on the fundus. Therefore, an assumed abnormal site is identified by the perimeter based on the abnormal site information based on the tomographic image referring to the database in which the abnormal site based on the tomographic image and the abnormal site by the perimeter are associated with each other, and the measurement positions on the fundus including the assumed abnormal site are set as the presenting region.

When the measurement result by the perimeter is reflected on the normal eye database used to analyze the tomographic image, a visual field database, which is used to evaluate whether or not the visual field is normal in the measurement information of the tomographic image, is built. Such a database can be used to evaluate whether or not the visual field is normal in the layer thickness information based on the tomographic image.

In the above explanation, the visual field measurement positions are automatically set based on the analysis result of the OCT device 100. In place of the automatic setting, an OCT map illustrating the two-dimensional analysis result of the fundus by the OCT device 100 (see the layer thickness map illustrated in FIG. 13) may be displayed on the monitor 31 so that the measurement points are set on the OCT map.

The examiner selects any desirable site on the OCT map by manipulating the operation input member such as a mouse. A measurement area comparable to the presenting region A may be set or the measurement points may be sequentially set by clicking.

In the above explanation, the OCT device 100 is provided separately from the perimeter, however, the OCT device 100 may be embedded in the optical system of the perimeter. For example, the optical coherence system of the OCT device 100 may be provided in addition to or in place of the visible-light imaging optical system.

In the above explanation, the analysis result is obtained by analyzing the tomographic image captured by the OCT device 100. As an alternative, the control unit 30 of the perimeter may analyze the tomographic image so that the analysis result of the tomographic image is obtained.

The active perimeter draws an isopter to measure the visual field by changing the conditions such as the target size and/or brightness. For example, a direction, a position, and/or a speed of the target movement are changed based on the set presenting region.

In the above explanation, the target presenting region during the visual field measurement is set according to the analysis result based on the tomographic image. As an alternative, the presenting region may be set according to the analysis result based on the fundus front image obtained by an apparatus that captures the fundus front image such as a fundus camera or SLO. Examples of the front image from which the analysis result is obtained are; a color fundus image, an infrared fundus image, and a fluorescent image.

As to the analysis of the front image, the abnormal site in the front image is detected in the form of a luminance variation (bright/dark) which does not occur in the case of a normal eye. Therefore, any site where the luminance level is higher or lower than a predetermined level is detected by image processing so that whether the site is abnormal and the position of the abnormal site are identified.

<Relationship Between Abnormal Positions in Visual Fields and Retinal Layers>

An examination position on the fundus by optical coherence tomography is preferably set so that the fundus tomographic image is obtained at a position related to an examination position on the fundus by the perimeter. Further, the examination position on the fundus by the perimeter is preferably set so that the visual field is examined at a position related to the examination position on the fundus by optical coherence tomography.

For example, the abnormal site in the fundus tomographic image and the abnormal site in the visual field are not always consistent with each other on the fundus. A retinal layer related to a visual field abnormality is possibly positionally shifted or deviated from an abnormal site actually detected in the visual field examination. When setting an examination position of the optical coherence tomography based on the result of the visual field examination or an examination position of the perimeter based on the result of tomographic image examination, the apparatus may set the examination position in consideration of any positional shift on the fundus between correlating abnormality positions of the visual field and the retinal layers.

The invention claimed is:

1. A control method of a fundus examination apparatus constructed as a perimeter for examining a fundus of an examinee's eye, the method including:
   controlling a monitor provided in the fundus examination apparatus as the perimeter to display a two-dimensional map pertinent to a two-dimensional analysis result of the fundus based on a tomographic image of the examinee's eye obtained by an optical coherence tomography device;
   setting an examination position in the fundus examination apparatus as the perimeter on the two-dimensional map displayed on the monitor; and
   subsequently controlling the fundus examination apparatus as the perimeter based on the set examination position to examine the fundus by visual field measurement.

2. The control method as claimed in claim 1, wherein the monitor is controlled to display chronological variations of a first parameter based on examination data obtained by the optical coherence tomography device and a second parameter based on examination data obtained by the fundus examination apparatus as the perimeter at once in a graphical representation.

3. The control method as claimed in claim 1, wherein a layer thickness map of the fundus of the examinee's eye is displayed as the two-dimensional map.

4. The control method as claimed in claim 1, wherein the examination position is set on the two-dimensional map based on an operation signal output from an operation input member manipulated by an examiner.

5. The control method as claimed in claim 1, wherein examination result data examined by the perimeter and analysis result data based on a tomographic image obtained by the optical coherence tomography device are associated with each other to provide a database, and
   target presenting conditions corresponding to the obtained analysis result data are obtained from the database.

6. The control method as claimed in claim 1, further including controlling operation of a target presenting unit configured to present stimulus targets in a visual field of the examinee's eye so that the stimulus targets are presented in turns at each measurement point corresponding to the set examination position to examine the visual field.

7. The control method as claimed in claim 1, further including displaying the two-dimensional map created based on layer information of the fundus in the tomographic image of the examinee's eye obtained by the optical coherence tomography device.

8. The control method as claimed in claim 1, further including displaying the two-dimensional map based on a comparison result obtained by comparing layer thickness information of the fundus based on the tomographic image of the examinee's eye obtained by the optical coherence tomography device to normal eye database.

9. The control method as claimed in claim 1, wherein the two-dimensional map is received from the optical coherence tomography device which is placed separately from the perimeter.

* * * * *